US011759354B2

(12) United States Patent
Pamichev et al.

(10) Patent No.: US 11,759,354 B2
(45) Date of Patent: *Sep. 19, 2023

(54) WORKING FLUID CASSETTE WITH HINGED PLENUM OR ENCLOSURE FOR INTERFACING HEAT EXCHANGER WITH INTRAVASCULAR TEMPERATURE MANAGEMENT CATHETER

(71) Applicant: Zoll Circulation, Inc., San Jose, CA (US)

(72) Inventors: Christo Petrov Pamichev, Cupertino, CA (US); Jeremy Thomas Dabrowiak, Santa Clara, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 693 days.

This patent is subject to a terminal disclaimer.

(21) Appl. No.: 16/026,427

(22) Filed: Jul. 3, 2018

(65) Prior Publication Data

US 2018/0311072 A1 Nov. 1, 2018

Related U.S. Application Data

(63) Continuation of application No. 14/676,672, filed on Apr. 1, 2015, now Pat. No. 10,022,265.

(51) Int. Cl.
*A61F 7/12* (2006.01)
*A61F 7/00* (2006.01)

(52) U.S. Cl.
CPC .............. *A61F 7/12* (2013.01); *A61F 7/0085* (2013.01); *A61F 2007/0054* (2013.01); *A61F 2007/0056* (2013.01); *A61F 2007/126* (2013.01)

(58) Field of Classification Search
CPC .. A61F 7/12; A61F 7/0085; A61F 2007/0056; A61F 2007/0054; A61F 2007/126
See application file for complete search history.

(56) References Cited

U.S. PATENT DOCUMENTS

| 1,459,112 A | 6/1923 | Mehl |
| 1,726,761 A | 9/1929 | Palmer |

(Continued)

FOREIGN PATENT DOCUMENTS

| CN | 101090685 A | 12/2007 |
| CN | 105377344 | 3/2016 |

(Continued)

OTHER PUBLICATIONS

American Urethane Inc., "Polyurethane Properties", available Oct. 12, 2010, http://web.archive.org/web/20101012211957/http://americanurethane.com/polyurethane-properties.html.

(Continued)

*Primary Examiner* — Joseph A Stoklosa
*Assistant Examiner* — Adam J Avigan
(74) *Attorney, Agent, or Firm* — ZOLL Circulation, Inc.

(57) ABSTRACT

An enclosure or plenum that supports a looped pump tube is hingedly connected to a framed thin-walled heat exchange bag through which working fluid from an intravascular heat exchange catheter flows. The frame with bag can be inserted between cold plates to exchange heat with the working fluid flowing through the bag. With the framed bag between the plates, the looped pump tube from the enclosure or plenum is receivable in the raceway of a peristaltic pump, which pumps working fluid through the system.

20 Claims, 7 Drawing Sheets

(56) References Cited

U.S. PATENT DOCUMENTS

| | | |
|---|---|---|
| 1,857,031 A | 5/1932 | Schaffer |
| 2,663,030 A | 12/1953 | Dahlberg |
| 2,673,987 A | 4/1954 | Upshaw et al. |
| 2,987,004 A | 6/1961 | Murray |
| 3,140,716 A | 7/1964 | Harrison et al. |
| 3,225,191 A | 12/1965 | Calhoun |
| 3,228,465 A | 1/1966 | Vadot |
| 3,369,549 A | 2/1968 | Armao |
| 3,425,419 A | 2/1969 | Dato |
| 3,504,674 A | 4/1970 | Swenson et al. |
| 3,726,269 A | 4/1973 | Webster |
| 3,744,555 A | 7/1973 | Fletcher et al. |
| 3,751,077 A | 8/1973 | Hiszpanski |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,181,245 A | 1/1980 | Garrett et al. |
| 4,298,006 A | 11/1981 | Parks |
| 4,459,468 A | 7/1984 | Bailey |
| 4,532,414 A | 7/1985 | Shah et al. |
| 4,552,516 A | 11/1985 | Stanley |
| 4,554,793 A | 11/1985 | Harding, Jr. |
| 4,558,996 A | 12/1985 | Becker |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,707,587 A | 11/1987 | Greenblatt |
| 4,731,072 A | 3/1988 | Aid |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,925,376 A | 5/1990 | Kahler |
| 4,941,475 A | 7/1990 | Williams et al. |
| 5,080,089 A | 1/1992 | Mason et al. |
| 5,092,841 A | 3/1992 | Spears |
| 5,103,360 A | 4/1992 | Maeda |
| 5,106,360 A | 4/1992 | Ishiwara et al. |
| 5,174,285 A | 12/1992 | Fontenot |
| 5,192,274 A | 3/1993 | Bierman |
| 5,195,965 A | 3/1993 | Shantha |
| 5,211,631 A | 5/1993 | Sheaff |
| 5,263,925 A | 11/1993 | Gilmore et al. |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,391,030 A | 2/1995 | Lee |
| 5,403,281 A | 4/1995 | O'Neill et al. |
| 5,433,588 A | 7/1995 | Monk et al. |
| 5,433,740 A | 7/1995 | Yamaguchi |
| 5,437,673 A | 8/1995 | Baust et al. |
| 5,458,639 A | 10/1995 | Tsukashima et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,706,889 A | 1/1998 | Bach et al. |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,746,585 A | 5/1998 | McDunn et al. |
| 5,759,017 A | 6/1998 | Patton et al. |
| 5,776,079 A | 7/1998 | Cope et al. |
| 5,788,647 A | 8/1998 | Eggers |
| 5,803,324 A | 9/1998 | Silberman |
| 5,837,003 A | 11/1998 | Ginsburg |
| 5,857,843 A | 1/1999 | Leason et al. |
| 5,862,675 A | 1/1999 | Scaringe et al. |
| 5,895,418 A | 4/1999 | Saringer |
| 5,908,407 A | 6/1999 | Frazee et al. |
| 5,957,963 A | 9/1999 | Dobak |
| 5,980,561 A | 11/1999 | Kolen et al. |
| 6,019,783 A | 2/2000 | Philips et al. |
| 6,042,559 A | 3/2000 | Dobak |
| 6,051,019 A | 4/2000 | Dobak |
| 6,059,825 A | 5/2000 | Hobbs et al. |
| 6,096,068 A | 8/2000 | Dobak et al. |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | DiMagno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak |
| 6,149,806 A | 11/2000 | Baer |
| 6,231,594 B1 | 5/2001 | Dae |
| 6,283,940 B1 | 9/2001 | Mulholland |
| 6,299,599 B1 | 10/2001 | Pham et al. |
| 6,338,727 B1 | 1/2002 | Noda et al. |
| 6,383,144 B1 | 5/2002 | Mooney et al. |
| 6,409,747 B1 | 6/2002 | Gobin et al. |
| 6,416,533 B1 | 7/2002 | Gobin et al. |
| 6,428,563 B1 | 8/2002 | Keller |
| 6,450,990 B1 | 9/2002 | Walker et al. |
| 6,464,666 B1 | 10/2002 | Augustine et al. |
| 6,464,716 B1 | 10/2002 | Dobak et al. |
| 6,527,798 B2 | 3/2003 | Ginsburg et al. |
| 6,530,946 B1 | 3/2003 | Noda et al. |
| 6,535,689 B2 | 3/2003 | Augustine et al. |
| 6,544,282 B1 | 4/2003 | Dae et al. |
| 6,551,309 B1 | 4/2003 | LePivert |
| 6,554,791 B1 | 4/2003 | Cartledge et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaiuolo et al. |
| 6,635,076 B1 | 10/2003 | Ginsburg |
| 6,673,098 B1 | 1/2004 | Machold et al. |
| 6,679,906 B2 | 1/2004 | Hammack et al. |
| 6,685,731 B2 | 2/2004 | Kushnir et al. |
| 6,685,733 B1 | 2/2004 | Dae et al. |
| 6,695,874 B2 | 2/2004 | Machold et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak |
| 6,743,201 B1 | 6/2004 | Dönig et al. |
| 6,799,342 B1 | 10/2004 | Jarmon |
| 6,843,800 B1 | 1/2005 | Dobak |
| 6,878,156 B1 | 4/2005 | Noda |
| 6,887,263 B2 | 5/2005 | Bleam et al. |
| 6,893,419 B2 | 5/2005 | Noda et al. |
| 6,969,399 B2 | 11/2005 | Schock et al. |
| 7,070,612 B1 | 7/2006 | Collins et al. |

(56) References Cited

U.S. PATENT DOCUMENTS

| | | |
|---|---|---|
| 7,104,769 B2 | 9/2006 | Davis |
| 7,140,850 B2 | 11/2006 | Otis |
| 7,510,569 B2 | 3/2009 | Dae et al. |
| 7,666,215 B2 | 2/2010 | Callister et al. |
| 7,713,036 B2 | 5/2010 | Kojima et al. |
| 7,822,485 B2 | 10/2010 | Collins |
| 7,846,193 B2 | 12/2010 | Dae et al. |
| 7,857,781 B2 | 12/2010 | Noda et al. |
| 7,892,269 B2 | 2/2011 | Collins et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,128,384 B2 | 3/2012 | Mou |
| 8,226,605 B2 | 7/2012 | Faries et al. |
| 8,272,857 B2 | 9/2012 | Norman et al. |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0145525 A1 | 10/2002 | Friedman et al. |
| 2002/0183692 A1 | 12/2002 | Callister |
| 2002/0198579 A1 | 12/2002 | Khanna |
| 2003/0036495 A1 | 2/2003 | Datta |
| 2003/0236496 A1 | 12/2003 | Samson et al. |
| 2004/0024437 A1* | 2/2004 | Machold ............... A61F 7/123 607/105 |
| 2004/0026068 A1 | 2/2004 | Schmidt et al. |
| 2004/0089058 A1 | 5/2004 | Haan et al. |
| 2004/0102825 A1 | 5/2004 | Daoud |
| 2004/0104018 A1 | 6/2004 | Hughes et al. |
| 2004/0143311 A1 | 7/2004 | Machold et al. |
| 2004/0175165 A1 | 9/2004 | Jusiak et al. |
| 2004/0210231 A1 | 10/2004 | Boucher et al. |
| 2005/0156744 A1 | 7/2005 | Pires |
| 2005/0234530 A1* | 10/2005 | Takashino ............... A61N 5/06 607/113 |
| 2006/0064146 A1 | 3/2006 | Collins |
| 2006/0069418 A1 | 3/2006 | Schock et al. |
| 2006/0122673 A1 | 6/2006 | Callister et al. |
| 2006/0210424 A1 | 9/2006 | Mallett et al. |
| 2006/0293734 A1 | 12/2006 | Scott et al. |
| 2007/0007640 A1 | 1/2007 | Harnden et al. |
| 2007/0076401 A1 | 4/2007 | Carrez et al. |
| 2007/0156006 A1 | 7/2007 | Smith et al. |
| 2007/0173759 A1 | 7/2007 | Augustine et al. |
| 2007/0191690 A1 | 8/2007 | Hasse et al. |
| 2007/0278155 A1* | 12/2007 | Lo ........................ A61M 1/166 210/646 |
| 2008/0230530 A1 | 9/2008 | Augustine et al. |
| 2008/0262409 A1 | 10/2008 | Derrico et al. |
| 2008/0267599 A1* | 10/2008 | Arnold ................ A61M 5/445 392/470 |
| 2008/0269676 A1 | 10/2008 | Bieberich et al. |
| 2009/0247963 A1 | 10/2009 | Bleam et al. |
| 2009/0299287 A1 | 12/2009 | Carson et al. |
| 2010/0036486 A1 | 2/2010 | Mazur |
| 2010/0129248 A1 | 5/2010 | Mou |
| 2011/0022136 A1 | 1/2011 | Scott et al. |
| 2011/0046551 A1 | 2/2011 | Augustine et al. |
| 2011/0137249 A1 | 6/2011 | Collins et al. |
| 2011/0184253 A1 | 7/2011 | Archer et al. |
| 2011/0196303 A1 | 8/2011 | Chan et al. |
| 2011/0208278 A1 | 8/2011 | Machold et al. |
| 2011/0213305 A1 | 9/2011 | Jönsson et al. |
| 2012/0100023 A1 | 4/2012 | Hanazuka et al. |
| 2012/0158103 A1 | 6/2012 | Bledsoe |
| 2013/0071270 A1 | 3/2013 | Zupp et al. |
| 2013/0331774 A1 | 12/2013 | Farrell et al. |
| 2014/0081202 A1 | 3/2014 | Tsoukalis |
| 2014/0277302 A1 | 9/2014 | Weber et al. |
| 2016/0287435 A1 | 10/2016 | Pamichev |

FOREIGN PATENT DOCUMENTS

| | | |
|---|---|---|
| DE | 19531935 A1 | 2/1997 |
| EP | 0663529 B1 | 5/1997 |
| GB | 1183185 A | 3/1970 |
| GB | 2040169 B | 3/1983 |
| GB | 2212262 A | 7/1989 |
| GB | 2383828 B | 6/2005 |
| JP | S61100243 A | 5/1986 |
| JP | H09215754 A | 8/1997 |
| JP | H10127777 A | 5/1998 |
| JP | H10305103 | 11/1998 |
| JP | 2004-504110 A | 2/2004 |
| JP | 2008531114 A | 8/2008 |
| JP | 2008539034 A | 11/2008 |
| JP | 2013-519849 A | 5/2013 |
| JP | 2019-205832 A | 12/2019 |
| WO | 1990001682 A1 | 2/1990 |
| WO | 9110414 A2 | 7/1991 |
| WO | 1993004727 A1 | 3/1993 |
| WO | 1994001177 A1 | 1/1994 |
| WO | 1994001177 A1 | 1/1994 |
| WO | 9503680 A1 | 2/1995 |
| WO | 1997025011 A1 | 7/1997 |
| WO | 1998024491 A1 | 6/1998 |
| WO | 1998040017 A2 | 9/1998 |
| WO | 2000010494 A1 | 3/2000 |
| WO | 2001013809 A1 | 3/2001 |
| WO | 2001026719 A1 | 4/2001 |
| WO | 2001064146 A1 | 9/2001 |
| WO | 2001076517 A2 | 10/2001 |
| WO | 2001083001 A1 | 11/2001 |
| WO | 2012175089 A1 | 12/2012 |
| WO | 2014160422 A1 | 10/2014 |
| WO | 2015119670 A1 | 8/2015 |
| WO | 2015122938 A1 | 8/2015 |

OTHER PUBLICATIONS

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

F.W. Behmann, E. Bontke, "Die Regelung der Wärmebildung bei künstlicher Hypothermie", Pflügers Archiv, Bd. 266, S. 408-421 (1958).

F.W. Behmann, E. Bontke, "Intravasale Kühlung", Pflügers Archiv, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dabrowiak et al., "Cold Plate Design in Heat Exchanger for Intravascular Temperature Managment Catheter and/or Heat Exhange Pad", filed history of related U.S. Appl. No. 14/675,504, filed Mar. 31, 2015.

Dabrowiak et al., "Fluid Cassette with Tensioned Polymeric Membranes for Patient Heat Exchange System" file history of related U.S. Appl. No. 14/180,613, filed Feb. 14, 2014. (1156.114).

Dabrowiak et al., "Fluid Cassette with Tensioned Polymeric Membranes for Patient Heat Exchange System" related pending U.S. Appl. No. 14/180,613, non-final office action dated May 19, 2016 (1156-114).

Dabrowiak et al., "Fluid Cassette with Tensioned Polymeric Membranes for Patient Heat Exchange System", related pending U.S. Appl. No. 14/180,613 final office action dated Jul. 15, 2016 (1156-114).

Dabrowiak et al., "Fluid Cassette with Tensioned Polymeric Membranes for Patient Heat Exchange System", related pending U.S. Appl. No. 14/180,613, applicant's response to non-final office action filed Jun. 1, 2016 (1156-114).

(56) References Cited

OTHER PUBLICATIONS

Dabrowiak et al., "Patient Heat Exchange System with Transparent Wall for Viewing Circulating Refrigerant" file history of related U.S. Appl. No. 14/275,202, filed May 13, 2014 (1156-117.CIP).
Dabrowiak et al., "Patient Heat Exchange System with Transparent Wall for Viewing Circulating Refrigerant", related pending U.S. Appl. No. 14/276,202 final office action dated Jul. 15, 2016.
Dabrowiak et al., "Patient Heat Exchange System with Transparent Wall for Viewing Circulating Refrigerant", related pending U.S. Appl. No. 14/276,202, non-final office action dated May 19, 2016 (1156-117.CIP).
Dabrowiak et al., "Patient Heat Exchange System with Transparent Wall for Viewing Circulating Refrigerant", related pending U.S. Appl. No. 14/276,202, applicant's response to non-final office action dated Jun. 1, 2016 (1156-117.CIP).
Dabrowiak et al., "Patient Heat Exchange System With Two and Only Two Fluid Loops", file history of related U.S. Appl. No. 14/180,719, filed Feb. 14, 2014 (1156.116).
Dabrowiak et al., "Patient Heat Exchange System with Two and Only Two Fluid Loops", related U.S. Appl. No. 14/180,719, Applicant's response to the Non-Final Office Action dated Sep. 7, 2016 (1156-116).
Dabrowiak et al., "Patient Heat Exchange System with Two and Only Two Fluid Loops", related U.S. Appl. No. 14/180,719, Non-Final Office Action dated Jun. 7, 2016. (1156-116).
Dabrowiak et al., "Patient Heat Exchange System with Two and Only Two Fluid Loops", related U.S. Appl. No. 14/180,719, Applicant's Response to the Non-Final Office Action filed Sep. 7, 2016. (1156-116).
Dabrowiak, "Heat Exchange System for Patient Temperature Control With Multiple Coolant Chambers for Multiple Heat Exchange Modalities", File History of related pending U.S. Appl. No. 15/332,519, filed Oct. 24, 2016. (1156-117.CON).
Dabrowiak, "Heat Exchange System for Patient Temperature Control with Multiple Coolant Chambers for Multiple Heat Exchange Modalities", file history of related U.S. Appl. No. 14/175,545, filed Feb. 7, 2014 (1156.117).
Dabrowiak, "Heat Exchange System for Patient Temperature Control with Multiple Coolant Chambers for Multiple Heat Exchange Modalities", related pending U.S. Appl. No. 14/175,545 applicants response to non-final office action dated May 2, 2016 (1156-117).
Dabrowiak, "Heat Exchange System for Patient Temperature Control with Multiple Coolant Chambers for Multiple Heat Exchange Modalities", related pending U.S. Appl. No. 14/175,545 non-final office action dated Feb. 12, 2016 (1156-117).
Dabrowiak, "Serpentine Heat Exchange Assembly for Removeable Engagement with Patient Heat Exchange System" file history of related U.S. Appl. No. 14/675,421, filed Mar. 31, 2015.
Hendricks et al., "Heat Exchange System for Patient Temperature Control with Easy Loading High Performance Peristaltic Pump", related U.S. Appl. No. 14/534,718, Non-Final Office Action dated Jul. 25, 2016. (1156-120).
Mazzone, "Proximal Mounting of Temperature Sensor in Intravascular Temperature Management Catheter", file history of related U.S. Appl. No. 14/675,452, filed Mar. 31, 2015 (1156.156).
Pistor et al., "Fluid Cassette with Polymeric Membranes and Integral Inlet and Outlet Tubes for Patient Heat Exchange System" file history of related U.S. Appl. No. 14/180,655, filed Feb. 14, 2014. (1156.115).
Pistor et al., "Fluid Cassette with Polymeric Membranes and Integral Inlet and Outlet Tubes for Patient Heat Exchange System", related pending U.S. Appl. No. 14/180,655, applicant's response to non-final office action file Jun. 1, 2016 (1156-115).
Pistor et al., "Fluid Cassette With Polymeric Membranes and Integral Inlet and Outlet Tubes for Patient Heat Exchange System", related U.S. Appl. No. 14/180,655, Final Office dated Sep. 8, 2016. (1156-115).
Pistor et al., "Fluid Cassette with Polymeric Membranes and Integral Intel and Outlet Tubes for Patient Heat Exchange System", related pending U.S. Appl. No. 14/180,655, non-final office action dated May 18, 2016 (1156-115).
Wittman-Regis, "Written Opinion of the International Searching Authority", dated Oct. 12, 2017, from counterpart PCT application PCT/US2016/025030.
EP European Search Report in European Appln. No. 21177713.1, dated Oct. 25, 2021, 10 pages.

\* cited by examiner

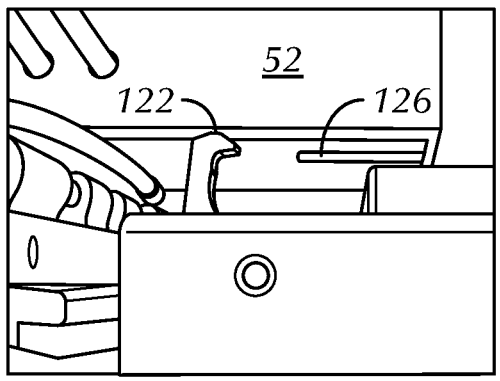 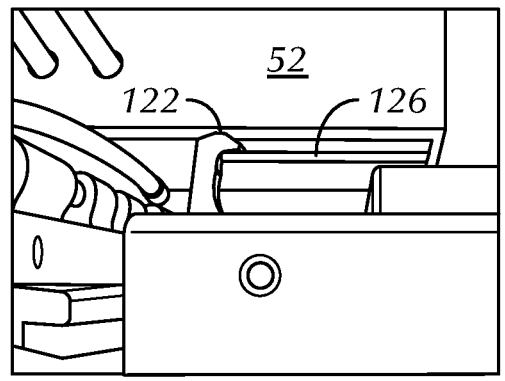
FIG. 9  FIG. 10
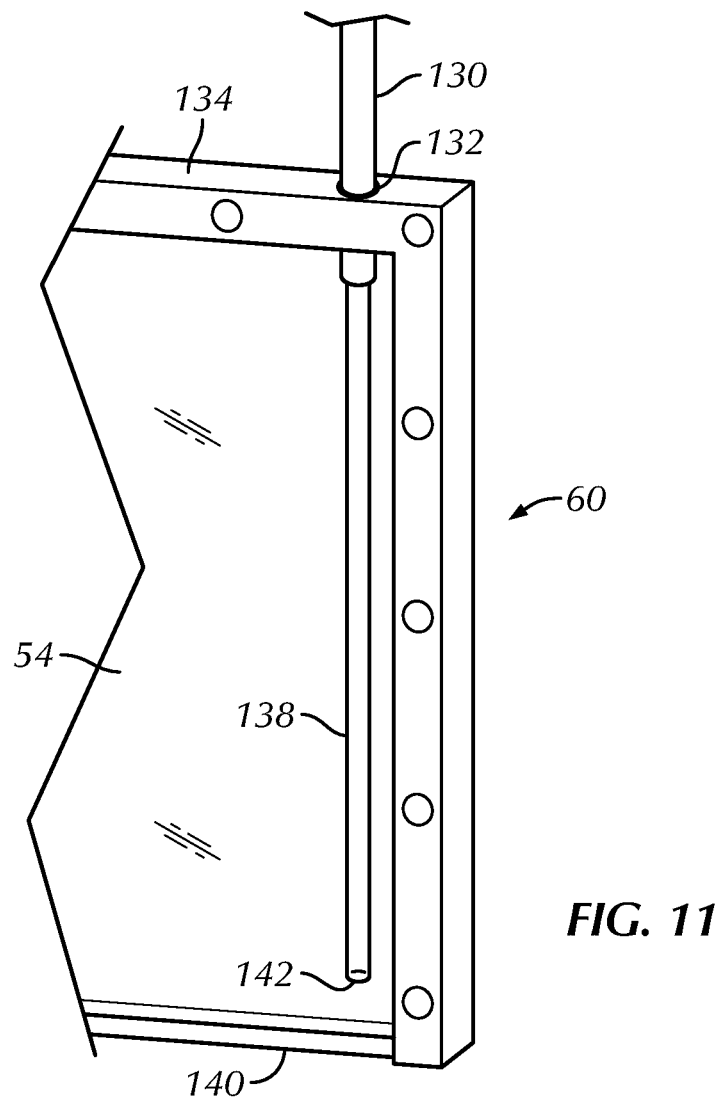
FIG. 11

WORKING FLUID CASSETTE WITH HINGED PLENUM OR ENCLOSURE FOR INTERFACING HEAT EXCHANGER WITH INTRAVASCULAR TEMPERATURE MANAGEMENT CATHETER

TECHNICAL FIELD

The present application relates generally to heat exchange systems for patient temperature control with working fluid cassettes.

BACKGROUND

Patient temperature control systems have been introduced to prevent fever in patients in the neuro ICU due to suffering from sub-arachnoid hemorrhage or other neurologic malady such as stroke. Also, such systems have been used to induce mild or moderate hypothermia to improve the outcomes of patients suffering from such maladies as stroke, cardiac arrest, myocardial infarction, traumatic brain injury, and high intracranial pressure. Examples of intravascular heat exchange catheters are disclosed in U.S. Pat. Nos. 7,914,564, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, 8,888,729, and USPPs 2013/0178923, 2013/0079855, 2013/0079856, 2014/0094880, 2014/0094882, 2014/0094883, all of which are incorporated herein by reference.

External patient temperature control systems may be used. Such systems are disclosed in U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference.

In general, in all of the intravascular and external patient temperature control solutions, the temperature of the working fluid flowing through the catheter or pad is regulated by a heat exchange console based on feedback provided by the patient's actual body temperature, typically core body temperature as may be variously measured rectally, esophageally, tympanic ear temperature, blood temperature in, e.g., the vena cava, etc. The working fluid temperature is regulated by thermally coupling the working fluid to heating and/or cooling elements in the console. In many cases, the working fluid is forced in a closed fluid circuit path (including the console and the catheter or pad) by a peristaltic pump acting on tubing, e.g., pump tubing or IV tubing, in the fluid circuit path.

SUMMARY

The following patent applications are hereby incorporated by reference herein in their entirety, Ser. No. 14/534,718, filed Nov. 6, 2014, and filed concurrently herewith.

As understood herein, it is desirable to provide a fast and easy way to interconnect an intravascular heat exchange catheter or external pad with a heat exchanger.

Accordingly, a device is provided which includes a thin-walled bag supported by a frame. The bag with frame is receivable between heat exchange plates such that heat can be exchanged between working fluid flowing through the bag and at least one of the heat exchange plates. A plenum or enclosure is connected to the frame. The plenum or enclosure supports a pump tube in fluid communication with the bag. The pump tube may be configured, for example in a loop, to engage a raceway or channel of a pump so that the pump can urge against the pump tube to circulate working fluid.

The plenum or enclosure may be hingedly connected to the frame for movement between a shipping position, in which an open or closed bottom side of the plenum or enclosure is parallel to the frame and is closely spaced from the bag, and an operating position, in which the bottom side is perpendicular to the frame. In some examples, a return tube is configured for carrying working fluid from an intravascular heat exchange catheter or external heat exchange pad to the bag.

If desired, a reservoir may be in the plenum or enclosure, or be a part of the plenum or enclosure, for receiving working fluid from the bag. In this example, the pump tube can receive working fluid from the reservoir. Also, a damper or dampener tube may be in fluid communication with the pump tube for receiving working fluid from the pump tube. The dampener tube may be configured with one or more pulse dampening loops or may be a straight or substantially straight length tube. Still further, a supply tube can be in fluid communication with the dampener tube for conveying working fluid to an intravascular heat exchange catheter or external heat exchange pad. In certain embodiments, the dampener may be in a form other than a tube. The dampener may be any pulse dampener, e.g., a dampener tube, damper or other device that absorbs the shock caused by a change in the direction or the speed of fluid flow within the tubes or other shock created by the pump's action. Other examples of dampeners include but are not limited to foam and air dampeners.

In some examples, working fluid from the return tube passes through an entry tube in a top rail of the frame to enter the bag. The entry tube has a first diameter and terminates proximate to the top rail so that working fluid enters the bag proximate the top rail. A drain tube extends through the entry tube toward a bottom rail of the frame that is opposite to and parallel with the top rail, with the drain tube terminating in an opening proximate to or remaining close to the bottom rail. The drain tube can be used for emptying the bag by reversing the pump to withdraw working fluid from the bag through the drain tube.

In another aspect, a device includes a plenum or enclosure that supports a looped pump tube, and a framed thin-walled heat exchange bag connected to the plenum or enclosure. The thin-walled heat exchange bag is for holding working fluid from an intravascular heat exchange catheter or external heat exchange pad, and is configured for insertion between opposed plates to effect heat exchange between the plates and working fluid flowing through the bag. When the framed thin-walled heat exchange bag is between the plates, the looped pump tube from the plenum or enclosure is receivable in or may be positioned in a raceway or channel of a peristaltic pump.

In another aspect, a method includes engaging a loop of a pump tube supported by a plenum or enclosure with a raceway or channel of a peristaltic pump, and disposing a heat exchange bag that depends downwardly from the plenum or enclosure between opposed plates of a heat exchanger.

The details of the various embodiments described herein, both as to their structure and operation, can best be under-

BRIEF DESCRIPTION OF THE DRAWINGS

FIG. 9 is a perspective view showing the cassette with pump assembly having a rotor in the load position;

FIG. 10 is a perspective view showing the cassette with pump assembly having a rotor in the lock (operational) position; and FIG. 11 a perspective view of an example cassette embodiment showing a drain tube for the thin-walled heat exchange bag, with portions of the frame broken away for clarity and with the plenum removed for ease of disclosure.

DETAILED DESCRIPTION

Figure 1:
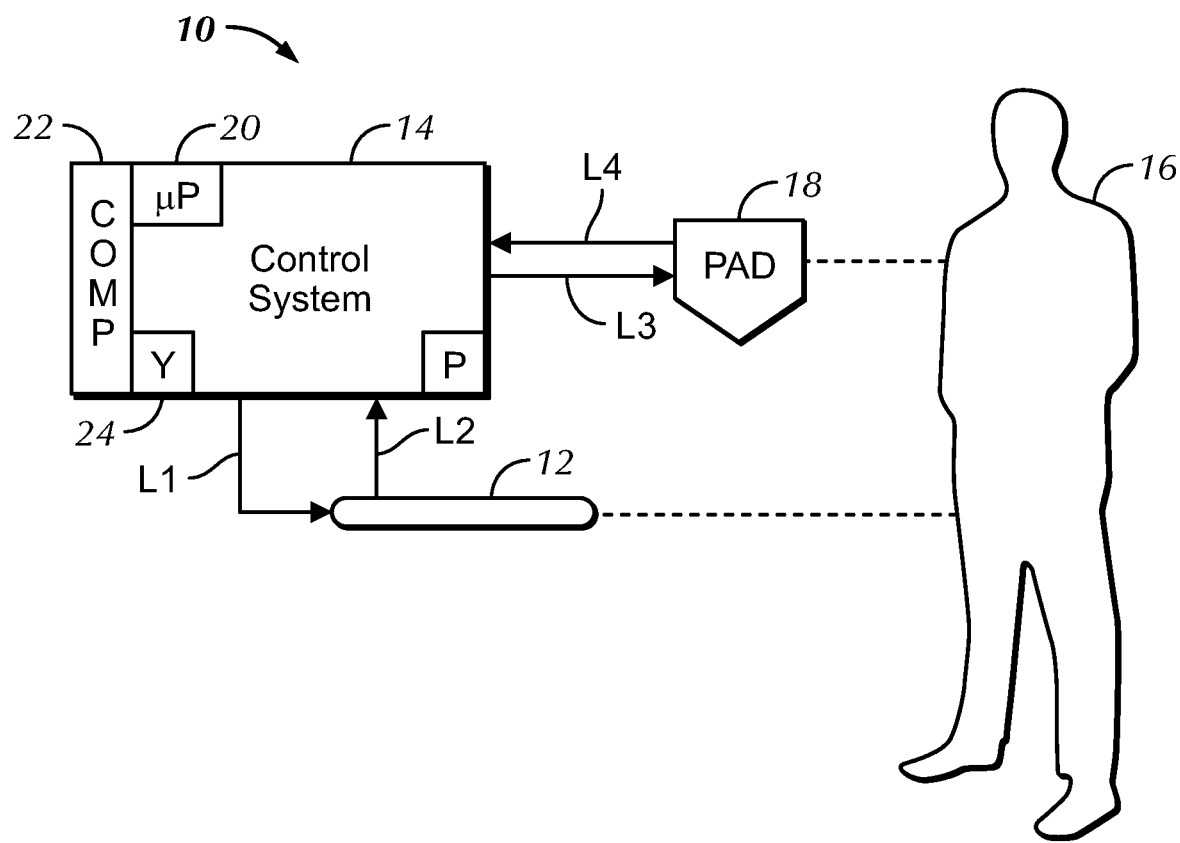
FIG. 1 is a schematic view of a non-limiting system in accordance with one embodiment.

Referring initially to FIG. 1, in accordance with present principles, a system 10 may include an intravascular heat exchange catheter 12 controlled by a control system 14 to control patient temperature, e.g., to prevent the patient 16 from becoming febrile or to induce therapeutic hypothermia in the patient 16. In the catheter, working fluid or a coolant such as but not limited to saline circulates (typically under the influence of a pump "P" in the control system) in a closed loop from the control system 14, through a fluid supply line L1, through the catheter 12, and back to the system 14 through a fluid return line L2, such that no working fluid or coolant enters the body. While certain preferred catheters are disclosed herein, it is to be understood that other catheters can be used in accordance with present principles, including, without limitation, any of the catheters disclosed above or in the following U.S. patents, all incorporated herein by reference: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149.673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, 8,888,729, 5,486,208, 5,837,003, 6,110,168, 6,149,673, 6,149,676, 6,231,594, 6,264,679, 6,306,161, 6,235,048, 6,238,428, 6,245,095, 6,251,129, 6,409,747, 6,368,304, 6,338,727, 6,299,599, 6,287,326, 6,126,684, 7,211,106 and USPPs 2013/0178923, 2013/0079855, 2013/0079856, 2014/0094880, 2014/0094882, 2014/0094883, all of which are incorporated herein by reference. The catheter 12 may be placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by the control system 14 to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia. The pad 18 may receive working fluid from the system 14 through a fluid supply line L3, and return working fluid to the system 14 through a fluid return line L4. The pump "P" may be a peristaltic pump which may engage any one of the lines L1-L4, which are typically plastic or other material IV lines, to urge working fluid through the lines through peristalsis.

The control system 14 may include one or more microprocessors 20 receiving target and patient temperatures as input and controlling, among other things, the pump "P" and a refrigerant compressor 22 and/or a bypass valve 24 that can be opened to permit refrigerant to bypass a condenser.

Figure 2:
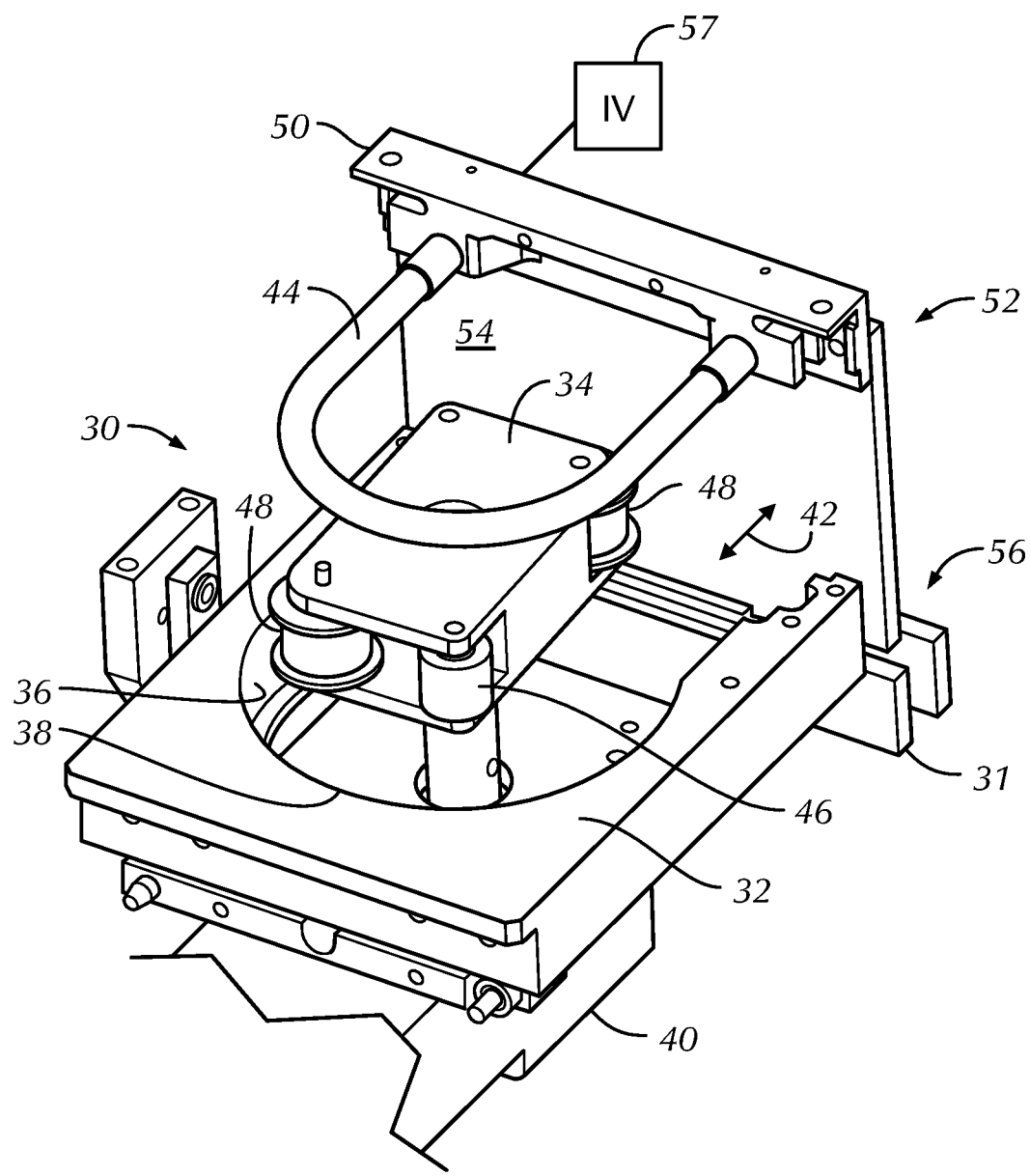
FIG. 2 is an exploded perspective view of an example pump with cassette.

Turning now to FIG. 2, an example of the pump "P" in FIG. 1 is shown and generally designated 30. It is to be understood that the pump assembly shown in FIG. 2 is coupled to cold plates 31 (shown schematically in FIG. 2) between which the below-described heat exchange or cassette bag is positioned to exchange heat with working fluid flowing through the bag to and from the catheter 12 or pad 18. Example details of the interplay between the cassette bag and cold plates are disclosed in U.S. patent application Ser. No. 14/180,719, filed Feb. 14, 2014, incorporated herein by reference.

The pump 30 includes a rigid, preferably metal or hard plastic raceway or channel housing 32 and a rotor 34. The raceway housing 32 may be formed from one or more blocks of material as shown and has an inner arcuate surface 36 which may have a substantially constant radius of curvature. In some examples, the arcuate surface 36, which defines a midpoint 38 between its two ends, can extend through an arc of at least one hundred eighty degrees (180°) (e.g., where two drive rollers are used) and may extend through an arc of between one hundred eighty degrees (180°) and two hundred seventy degrees (270°). In the example shown, the arcuate surface 36 extends, from one end to the other end, through an arc of greater than 200°. For example, the arc may be about 210° to 230°. In certain embodiments, the arcuate surface of a raceway may extend through an arc equal to 360° divided by n, where n is equal to the number of drive rollers mounted on or near a rotor which is rotated relative to the raceway.

A motor 40 rotates the rotor 34 relative to the raceway 32. As well, the rotor 34 is movable translationally and/or rotationally relative to the raceway 32 as shown by the arrows 42 between a pump position, in which the rotor 34 is spaced from the midpoint 38 of the inner surface 36 of the raceway 32 a first distance, and a tube load position, in which the rotor 34 is spaced from the midpoint 38 a greater, second distance. In the pump or operating position, rollers on the rotor 34 urge against a tube such as an IV tube that is disposed between the rollers and the raceway 32. In the tube load position, the rotor 34 is sufficiently spaced from the raceway 32 to permit a tube 44 to be disposed between the raceway and rotor and to be removed therefrom, e.g., by hand. The rotor 34 may be moved translationally and/or rotationally by, e.g., an actuator stepper motor, or by a manually-actuated lever linkage, or other appropriate mechanism or means.

Mounted on the rotor 34 are one or more rollers to urge against the tube 44 to pump fluid through the tube. In the example shown in FIG. 2, the rotor 34 is defined in part by a rectilinear, non-square body, and on or near each corner of the body a roller is mounted, e.g., rotatably mounted to the rotor body. In the example, at one set of opposed corners on the body, drive rollers 46 are respectively mounted (only one drive roller shown in the perspective of FIG. 2), whereas at the other set of opposed corners on the body, guide rollers 48 are respectively mounted. Thus, between the drive rollers 46 are guide rollers 48.

As shown in FIG. 2, the drive roller 46 has a cylindrical outer surface, and at least a portion of the outer surface is configured to urge against the tube 44. The outer surface of the example drive roller may be a single smooth cylinder and/or it may or may not have one or more flanges having peripheries extending beyond the cylindrical outer surface. In contrast, the guide roller 48 also has a cylindrical outer surface but in addition includes top and/or bottom flanges defining respective peripheries extending beyond the cylindrical outer surface of the guide roller such that the tube 44 can be received on the cylindrical outer surface of the guide roller between the flanges when the rotor 34 is in the pump position and is rotated. In the example shown, two and only two drive rollers 46 and two and only two guide rollers 48 are provided, but any number of drive and/or guide rollers may be utilized. In certain embodiments, the drive roller or guide roller may have a non-cylindrical or partially cylindrical outer surface.

The tube 44 may be configured as a loop, with the ends of the loop engaged with a plenum 50 (while certain embodiments below refer to a plenum, an enclosure, compartment or other like component may be utilized) of a working fluid cassette, generally designated 52. The plenum 50 is hingedly engaged with or coupled to a framed cassette bag 54. Example details of the framed bag 54 are discussed further below. Additional example details that may be used with the working fluid cassette 52 are shown and described in U.S. patent application Ser. Nos. 14/180,613 and 14/180,655, filed Feb. 24, 2014 and incorporated herein by reference. Such a cassette can be engaged with structure in the control system 14 to exchange heat with working fluid flowing through the cassette 52 and tube 44 and being circulated by the pump 30 shown and described herein to and from a heat exchange member such as the catheter 12 and/or pad 18 through, e.g., the lines L1 and L2 shown in FIG. 1. Note that the plenum 50 may also be connected via an IV line to an external working fluid reservoir such as an IV bag 57.

When the bag 54 is disposed vertically between the cold plates 31 as described in the above-referenced U.S. patent application Ser. No. 14/180,719, the plenum 50 can be locked into place as the rotor of the pump 30 moves into the pump or operating position as described further below.

In examples, the cassette bag 54 may be made of two polymeric membranes closely spaced from each other and supported by a frame that is slidably engageable with a slot 56 on a cold plate assembly that supports the pump of FIG. 2. In certain embodiments, the frame may be made in halves that are positioned to sandwich or securely support a border portion of the cassette bag 54 therebetween. In certain variations, the cold plate assembly may include receptacles for receiving a portion of the cassette as it is inserted into the slot 56. The receptacles may be keyed or each receptacle may have a different shape which corresponds to the shapes or configuration of a portion the cassette or cassette frame received by the receptacles. These features would help ensure that the cassette is inserted between the cold plates in the correct or proper orientation, providing guidance to a user. A working fluid chamber is established between the membranes. In one example, each membrane is no more than three mils (0.003") thick and may be between one mil and three mils in thickness (0.001→-0.003"), inclusive. In certain embodiments, each membrane may be between one mil and five mils in thickness (0.001"-0.005"). The example preferred membranes are more or less square, with the length of top and bottom edges of the example membranes being approximately equal (within ±10% and more preferably within ±5%) of the lengths of the left and right edges of the membranes. Thus, the working fluid chamber between the membranes may also be rectilinear and there may be no obstructions between the membranes, meaning the Working fluid chamber is a complete rectilinear, more or less square chamber. In preferred examples, the membranes are stretched under tension during assembly to the frame.

Figure 3:
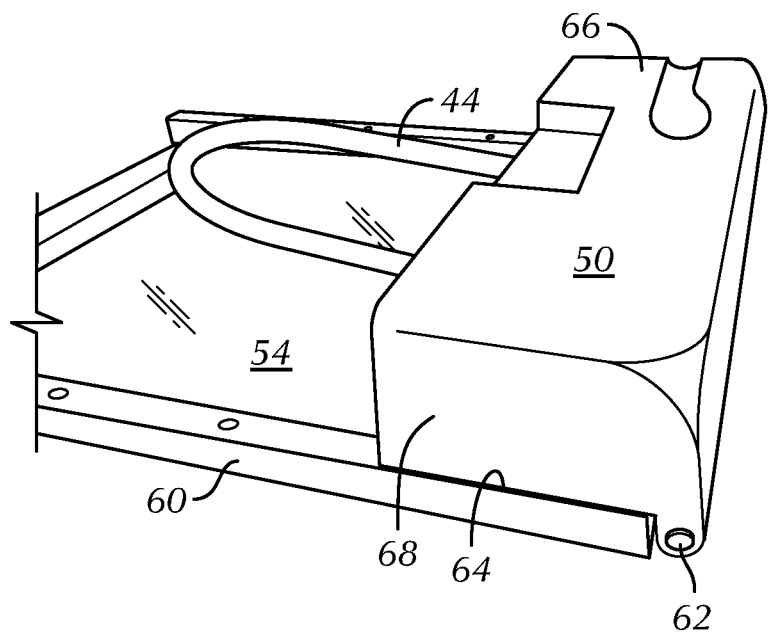
FIG. 3 is a perspective view of an example cassette with the plenum in the shipping position.
Figure 4:
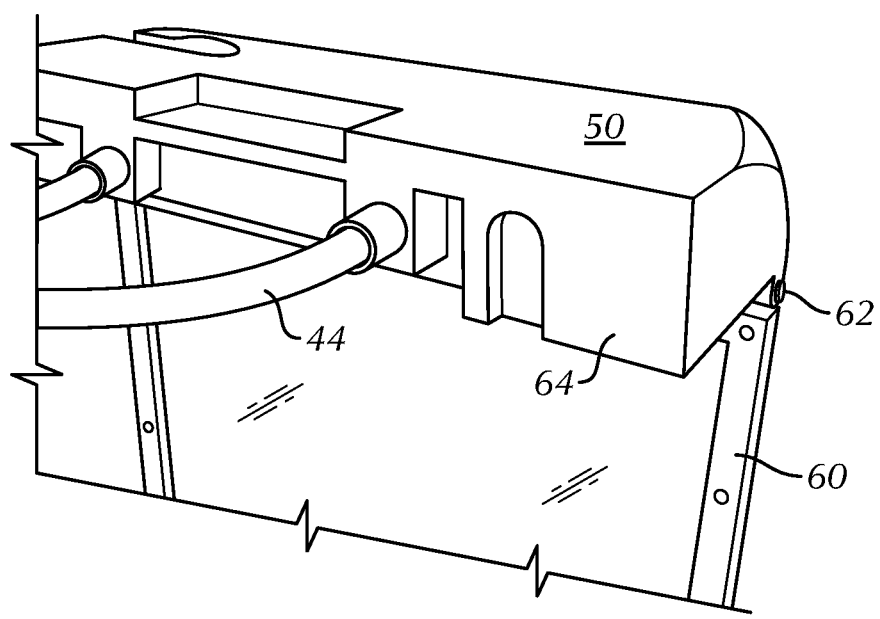
FIG. 4 is a perspective view of an example cassette with the plenum in the operating position.
Figure 5:
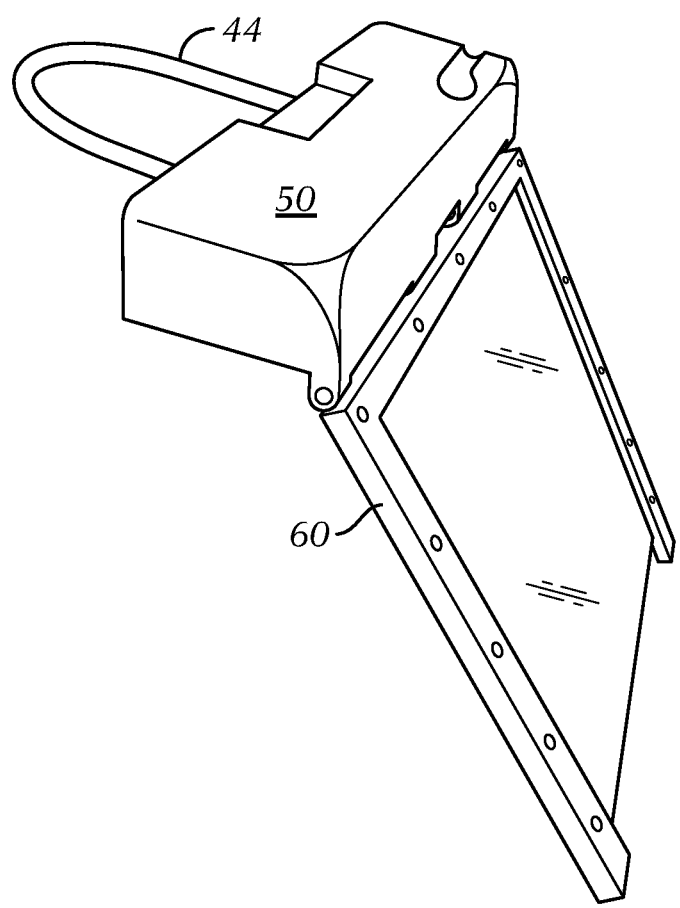
FIG. 5 is a perspective view of an example cassette with the plenum hinged or rotated beyond the operating position.

FIGS. 3 and 4 show that the cassette bag 54 is bounded by a frame 60, and that the plenum 50 is joined to the frame 60 at a hinge 62 for movement between a shipping position (FIG. 3), in which an open bottom side 64 of the plenum 50 is parallel to the frame 60 and is closely spaced from the bag 54, and an operating position (FIG. 4), in which the open bottom side 64 is rotated 90° from the shipping position so that it is perpendicular or close to perpendicular to the frame 60. A hinged plenum or enclosure 50 provides several advantages and benefits. For example, it allows the cassette to easily assume a more compact shipping configuration or operating position. Positioning the plenum or enclosure perpendicular to or angled relative to the frame provides for an increased angular tolerance between the cassette and the pump when the cassette is positioned within the cold plates and coupled to the pump. Also, the perpendicular or angled configuration allows a user to have top view of the pump and the cold plate simultaneously when the cassette is positioned in between the cold plates and the tube 44 is coupled to the pump. While the bottom side 64 of the plenum or enclosure is shown as having an open configuration, in certain embodiments, the bottom, side may be closed or at least a portion of the bottom side may be closed. The bottom side 64 is generally rectangular and extends the width of the frame 60 as shown. In some examples the plenum 50 or enclosure may be pivoted or rotated beyond the operating position to establish an obtuse angle with respect to the frame 60 as shown in FIG. 5. As shown best in FIG. 3, the bottom side 64 is opposed by a complementarily-shaped closed or open top side 66 and is spaced therefrom by sidewalls 68.

Figure 6:
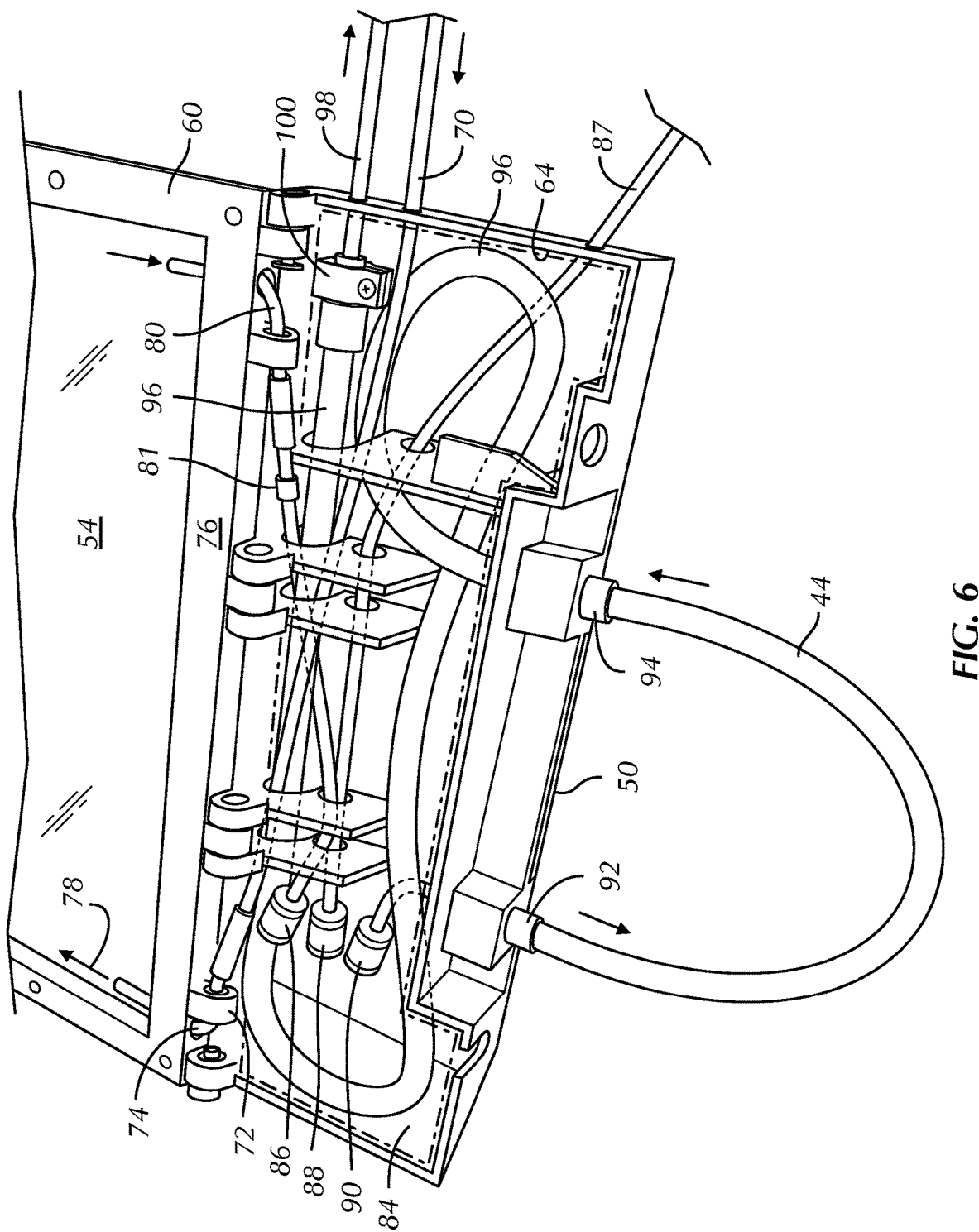
FIG. 6 is a perspective view of the interior of the plenum as would be seen from the bottom of the plenum when disposed for operating.

FIG. 6 shows the interior of an open bottom side 64 of the plenum 50. A return tube 70 carrying working fluid from the catheter 12 or heat exchange pad 18 enters one of the sides 68 of the plenum 50. The return tube 70 passes across the plenum 50 to the opposite side, where it is supported by a support or bearing 72, entering an inlet opening 74 of a top rail 76. The return tube 70 ends, as further discussed below in reference to FIG. 11, just below the top rail 76 in the bag 54. Working fluid flows out of the return tube and into the bag 54 as indicated by the arrow 78, back across the bag, and out of an exit tube 80 that extends through an opening in the top rail 76.

The exit tube 80 in turn enters an enclosed working fluid reservoir 84 in the plenum 50, e.g., through an entry port connector 86. The reservoir may be a separate container or manifold positioned within the enclosure or plenum or may be integral with the enclosure or plenum. The reservoir may collect or hold an amount of working fluid necessary or required to run the system. One or more level sensors may be provided in the reservoir 84 to generate a signal when the reservoir fluid level falls below a threshold. The signal can be used to activate a warning lamp or audio alarm. Note that the entry port connector 86 is located near the top of the reservoir 84 in the bottom view shown. Also, an IV bag line or tube 87 is connected to the reservoir 84 via an IV bag connector 88 to supply working fluid to the system from the IV bag 57 shown in FIG. 2. While the embodiments refer to an IV bag, other IV or working fluid sources may be used, e.g., a bottle, bag or other container. The reservoir 84 may be connected to the IV bag through a single line 87 used to deliver working fluid to the reservoir 84, e.g., during priming of the system and/or to compensate for thermal and other fluctuations of the working fluid's volume. The line 87 may also be used to evacuate air from the system and into the IV bag, and/or to bring the working fluid back into the IV bag during purging or draining of the system at the end of a procedure.

A single line or tube 87 in a closed fluid circuit path provides a sterile barrier or environment for the working fluid and also provides enhanced or improved convenience. Working fluid, e.g., saline, may be delivered through the line 87, and air may travel back up through the same line 87, in an opposite direction if desired, e.g., during priming, allowing for the delivery of two different fluids (e.g., water or saline and air) through the same line. The delivery of saline and air may not occur simultaneously and/or a filter may not be required. A closed fluid circuit path or closed loop system utilizing a single IV bag line or other fluid source line without a filter may work for up to 7 days, and in certain embodiments may work for more than 7 days. The pump described herein may operate in both directions, and the pump may be self-priming such that it can pump air and/or water.

Near the bottom of the reservoir 84, an outlet connector 90 establishes fluid communication between the working fluid in the reservoir 84 and the peristaltic tube 44 which extends through a tube exit opening 92 to engage the peristaltic pomp described above. The pump urges against the tube 44 to circulate working fluid in the pathway described herein. The tube 44 reenters the plenum 50 through a tube entry opening 94 to engage or be made integrally with a dampener tube 96. The tube 44 may connect to a downstream dampener or dampener tube directly or via an intermediate tribe or manifold.

As shown, the example dampener tube 96 has a larger diameter than the exit tube 80 and furthermore extends back and forth across the plenum 50 one or more or multiple times, e.g., being bent through one or more 180 degree loops as shown. Alternatively, the dampener tube may be partially or entirely located outside of the plenum, and or may be a straight or substantially straight length tube with no or minimal loops. The purpose of the dampener tube 96 is to dampen pulses in the working fluid caused by the peristaltic pumping action. The dampener tube 96 is joined to a smaller diameter working fluid supply tube 98 at a clamp-like joint 100. Working fluid is conveyed to the catheter 12 or pad 18 through the supply tube 98.

Figure 7:
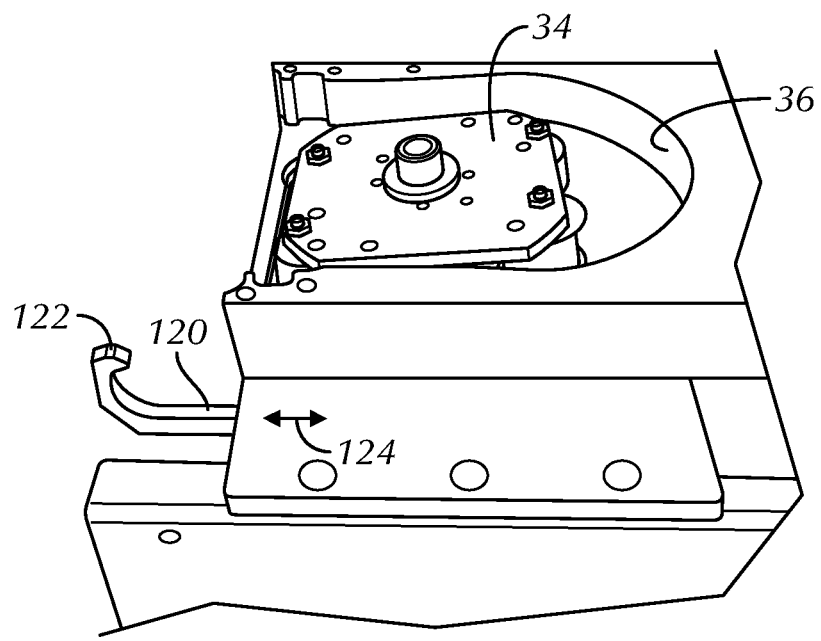
FIG. 7 is a perspective view of the pump assembly with the rotor in a load position.
Figure 8:
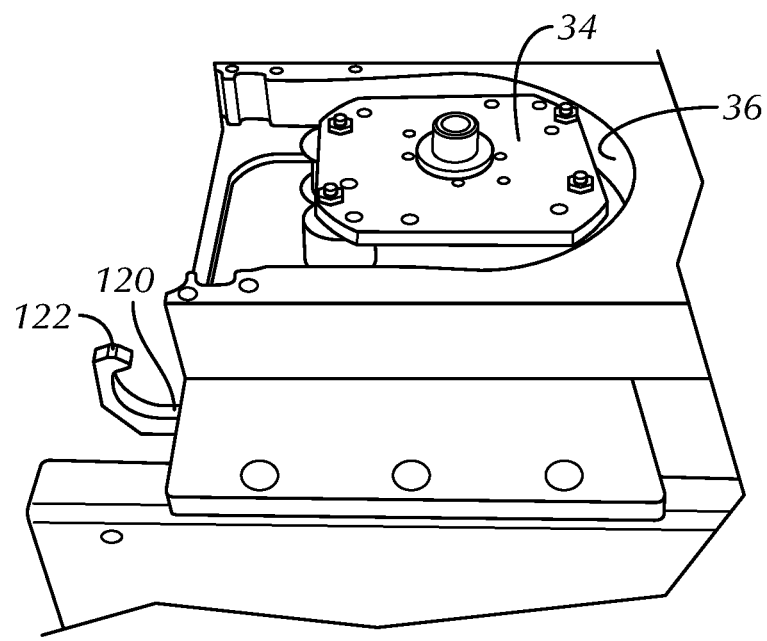
FIG. 8 is a perspective view of the pump assembly with the rotor in a lock (operational) position.

FIGS. 7-10 illustrate an example interlock that may be provided between the pump 30 and the cassette 52. FIGS. 7 and 9 illustrate the pomp assembly with the rotor 34 in the loading configuration or position and FIGS. 8 and 10 show the pump assembly with the rotor 34 in the lock (operating or pump) configuration or position.

In FIGS. 7 and 9, a horizontal locking bar 120 terminating in an upwardly-projecting engagement hook 122 is connected to a rotor carriage or motor mount, which supports the rotor 34, so that the locking bar 120 moves in the directions indicated by the arrows 124 as the rotor carriage or mount and rotor move as described in reference to FIG. 2. The rotor carriage or mount (and hence locking bar 120) are in the load position in FIGS. 7 and 9, in which the rotor 34 is distanced from the raceway or raceway surface 36 to allow the pump tube 44 of the cassette 52 to be engaged or placed in the space between the rotor 34 and the raceway. As shown in FIG. 9, an engagement shelf 126 or protrusion on the bottom of the cassette 52 is clear of the engagement hook 122 in this position, allowing the cassette 52 to be moved to position the pump tube 44 in the raceway 32.

In contrast, FIGS. 8 and 10 show that when the rotor carriage or mount and rotor 34 are moved to the lock, pump or operating position such that the pump rollers can urge the pump tube 44 against the raceway or raceway surface 36, the locking bar 120 also moves to a position in which the engagement hook 122 has moved onto the top surface of the engagement shelf 126, trapping the shelf 126 and, hence, the cassette 52 so that the cassette 52 cannot be withdrawn when in the rotor carriage or mount, the rotor, and the locking bar 120 with hook 122 are in the lock, pump or operating position.

FIG. 11 illustrates that in some examples, working fluid from the return tube 70 in FIG. 6 passes through the plenum 50 or enclosure (not shown in FIG. 11) to an entry tube 130 (which may be the same as or connected to the return tube). The entry tube 130 passes into an opening 132 in a top rail 134 of the cassette frame 60 to enter the bag 54. In the example shown, the entry tube 130 terminates in or just below (e.g., ¼→ below) the top rail 134 so that working fluid exists the entry tube 130 proximate to the top rail 134 and flows downwardly and across the bag 54.

A drain tube 138 with a smaller diameter than the entry tube 130 extends through the entry tube 130 as shown toward a bottom rail 140 of the frame 60 that is opposite to and parallel with the top rail 134. The drain tube 138 terminates in an opening 142 that is proximate to (e.g., within ¼→ or so of) the bottom rail 140. When working fluid is being circulated through the catheter 12 and bag 54 during patient temperature management operation, at least a portion of the working fluid being returned from the catheter 12 to the cassette 52 exits the larger diameter opening of the entry tube 130, near the top of the cassette 52, and at least a portion of the working fluid flows down and across the bag 54 to exchange heat with the plates between which the bag 54 is disposed.

When it is desired to drain the catheter and/or bag to facilitate withdrawal of the bag 54 from the plates, which can be impeded if the bag 54 remains full of working fluid, the pump may be reversed. This evacuates working fluid from bag 54 through the drain tube 138. The evacuation causes the bag material to collapse around the larger entry tube 130, leaving most of the suction at the opening 142 of the drain tube 138. The working fluid is pumped through the drain tube 138 back into the reservoir 84 in the plenum or enclosure and from there to the IV bag. When the catheter remains connected to the cassette 52, working fluid is also evacuated from the catheter. When the catheter is not connected prior to draining the bag 54, the connectors (typically Luer fittings) that connect catheter IV lines to the supply and return lines of the cassette may be simply connected together to close the fluid loop.

In certain embodiments, a check valve 81 (FIG. 6) may be placed on or in the line or tube between the heat exchange bag 54 and the reservoir 84 to prevent working fluid from moving from the reservoir 84 back to the heat exchange bag 54 during fluid evacuation or purging. Optionally, a check valve 81 may be placed inside the reservoir 84 to prevent working fluid from moving from the reservoir 84 back to the heat exchange bag 54 during fluid evacuation or purging. Such valves may ensure that the working fluid is evacuated and/or flows back to an IV bag or other container, such that the heat exchange bag may be properly drained and may be easily removed from between the heat exchange plates. Working fluid may also be evacuated or drained from the catheter, when the catheter is connected to the system, which results in a reduction in the diameter of the catheter such that the catheter may be removed from a patient. If desired, the catheter may be disconnected, such that only the heat exchange bag is drained or evacuated of working fluid. In other embodiments, a high pressure dampener may be utilized that provides fluctuations in the volume of working fluid, such that purging or draining of working fluid may be performed with or without a check valve.

In certain embodiments, when filling the cassette bag during priming, the pump can be started and stopped in short periods to allow air to vent back through the reservoir in the plenum or enclosure. The pump may also be reversed to speed up the movement of air back through the reservoir and/or to the IV bag or fluid source. A single line may be used for delivering liquid and/or air between the reservoir and the IV bag or fluid source, allowing air to be removed from the fluid path without requiring the use of either a two-lumened spike line which may be more difficult for the user to install, or a hydrophobic vent or other filter which allows air to escape but may break down over time causing working fluid to leak out of the system.

Components included in one embodiment can be used in other embodiments in any appropriate combination. For example, any of the various components described herein and/or depicted in the Figures may be combined, interchanged or excluded from other embodiments. "A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

While various embodiments of a WORKING FLUID CASSETTE WITH HINGED PLENUM OR ENCLOSURE FOR INTERFACING HEAT EXCHANGER WITH INTRAVASCULAR TEMPERATURE MANAGEMENT CATHETER are herein shown and described in detail, the scope of the present invention is to be limited by nothing other than the appended claims.

What is claimed is:

1. A device, comprising:
   a bag supported by a frame, the bag with frame being receivable between heat exchange plates such that heat can be exchanged between working fluid flowing through the bag and at least one of the heat exchange plates, wherein the frame includes first and second halves that support a border portion of the bag therebetween; and
   a plenum supporting a conduit in fluid communication with the bag, the conduit being configured to extend exteriorly of the plenum to engage a pump so that the pump can urge against the conduit to circulate working fluid, wherein working fluid from a heat exchange element is passable through an entry tube in a first rail of the frame to enter the bag, the entry tube having a first diameter and terminating proximate to the first rail so that working fluid enters the bag proximate the first rail, and the device further comprises a drain tube extending toward a second rail of the frame that is opposite to and parallel with the first rail, the drain tube terminating proximate to the second rail, the drain tube being useful for emptying the bag by reversing the pump to withdraw working fluid from the bag through the drain tube, wherein the plenum is rotatably coupled to the frame for moving between a shipping position and an operating position, in which the plenum moves from a first configuration for the shipping position to a second configuration for the operating position.

2. The device of claim 1, wherein the plenum is hingedly connected to the frame for movement between the shipping position, in which the first configuration comprises an open bottom side of the plenum being parallel to the frame and is closely spaced from the bag, and the operating position, in which the second configuration comprises the open bottom side being perpendicular to the frame.

3. The device of claim 1, comprising a return tube configured for carrying working fluid from a heat exchange catheter or external heat exchange pad to the bag.

4. The device of claim 3, comprising a reservoir in the plenum for receiving working fluid from the bag.

5. The device of claim 4, wherein the conduit is configured to receive working fluid from the reservoir.

6. The device of claim 1, comprising a dampener tube in fluid communication with the conduit for receiving working fluid from the conduit, the dampener tube being configured to dampen pulses in the working fluid.

7. The device of claim 6, wherein the dampener tube is configured with one or more dampening loops.

8. The device of claim 6, comprising a supply tube in fluid communication with the dampener tube for conveying working fluid to an intravascular heat exchange catheter or external heat exchange pad.

9. The device of claim 1, wherein the drain tube extends through the entry tube.

10. The device of claim 1, wherein the conduit supported by the plenum is in a superposed relation to the bag when the plenum is in the shipping position.

11. A device comprising:
    an enclosure in which is disposed a pump tube;
    an assembly comprising a heat exchange bag coupled to the enclosure, the heat exchange bag for holding working fluid from an intravascular heat exchange catheter or external heat exchange pad, the heat exchange bag being configured for insertion between opposed plates to effect heat exchange between the opposed plates and working fluid flowing through the heat exchange bag, wherein when the heat exchange bag is between the opposed plates, the pump tube from the enclosure is receivable in a peristaltic pump, wherein working fluid from the intravascular heat exchange catheter or external heat exchange pad is configured to pass through an entry tube to enter the heat exchange bag; and
    a dampener tube in fluid communication with the pump tube for receiving working fluid from the pump tube, the dampener tube being configured to dampen pulses in the working fluid, wherein the enclosure is rotatably coupled to the assembly for movement between a shipping position and an operating position, in which the enclosure moves from a first configuration for the shipping position to a second configuration for the operating position, wherein at least a portion of the dampener tube extends exteriorly of the enclosure.

12. The device of claim 11, wherein the enclosure is hingedly connected to the assembly for movement between the shipping position, in which the first configuration comprises an open bottom side of the enclosure being parallel to the assembly and being closely spaced from the heat exchange bag, and an operating position, in which the second configuration comprises open bottom side being perpendicular to the assembly.

13. The device of claim 11, comprising a reservoir in the enclosure for receiving working fluid from the heat exchange bag.

14. The device of claim 13, wherein the reservoir is in fluid communication with an IV fluid source via a single IV line, and wherein the device provides a closed fluid circuit path where liquid and air are configured to flow in opposite directions through the single IV line or other line.

15. The device of claim 11, wherein the pump tube is in fluid communication with a reservoir in the enclosure to receive working fluid from the reservoir.

16. The device of claim 11, comprising:
a drain tube extending toward a rail of the assembly that is distanced from the entry tube, the drain tube being useful for emptying the heat exchange bag by reversing the peristaltic pump to withdrawn working fluid from the heat exchange bag through the drain tube.

17. The device of claim 16, wherein the dampener tube is configured with one or more pulse dampening loops.

18. The device of claim 11, comprising a supply tube in fluid communication with the dampener tube for conveying working fluid to an intravascular heat exchange catheter or external heat exchange pad.

19. A device, comprising:
a bag supported by a frame, the bag with frame being receivable between heat exchange plates such that heat can be exchanged between working fluid flowing though the bag and at least one of the heat exchange plates; and
a plenum hingedly coupled to the frame and supporting a conduit in fluid communication with the bag, the conduit being configured to engage a pump so that the pump can urge against the conduit to circulate working fluid, wherein working fluid from a heat exchange element is passable through an entry tube in a first rail of the frame to enter the bag, the entry tube having a first diameter and terminating proximate to the first rail so that working fluid enters the bag proximate the first rail.

20. The device of claim 19, comprising:
a dampener tube in fluid communication with the conduit for receiving working fluid from the conduit, the dampener tube being configured to dampen pulses in the working fluid.

\* \* \* \* \*

UNITED STATES PATENT AND TRADEMARK OFFICE
CERTIFICATE OF CORRECTION

PATENT NO. : 11,759,354 B2
APPLICATION NO. : 16/026427
DATED : September 19, 2023
INVENTOR(S) : Christo Petrov Pamichev and Jeremy Thomas Dabrowiak It is certified that error appears in the above-identified patent and that said Letters Patent is hereby corrected as shown below:

On the Title Page

Page 3, Column 2, Line 1 item [56] delete "Predue" and insert --Perdue--

Page 3, Column 2, Line 18 item [56] delete "Managment" and insert --Management--

Page 3, Column 2, Line 18 item [56] delete "Exhange" and insert --Exchange--

In the Specification

Column 3, Line 55 delete "6,149.673," and insert --6,149,673,--

Column 6, Line 9 delete "(0.001→-0.003")," and insert --(0.001"-0.003"),--

Column 6, Line 18 delete "Working" and insert --working--

Column 6, Line 43 delete "bottom," and insert --bottom--

Column 7, Line 42 delete "pomp" and insert --pump--

Column 7, Line 48 delete "tribe" and insert --tube--

Column 7, Line 64 delete "pomp" and insert --pump--

Column 8, Line 35 delete "¼→below)" and insert --within 1/4"--

Column 8, Line 43 delete "within ¼→" and insert --within 1/4"--

Signed and Sealed this
Thirteenth Day of August, 2024

*Katherine Kelly Vidal*

Katherine Kelly Vidal
*Director of the United States Patent and Trademark Office*